United States Patent [19]

Pettigrew et al.

[11] Patent Number: 5,024,090

[45] Date of Patent: Jun. 18, 1991

[54] LOOSE ROCK DETECTOR

[75] Inventors: Michel J. Pettigrew; David B. Rhodes; Eric G. Lux; Victor A. Mason, all of Deep River, Canada

[73] Assignee: HDRK Mining Research Limited, Copper Cliff, Canada

[21] Appl. No.: 407,866

[22] Filed: Sep. 15, 1989

[30] Foreign Application Priority Data

Sep. 30, 1988 [CA] Canada ................................ 579030

[51] Int. Cl.5 ............................................. G01N 3/30
[52] U.S. Cl. ...................................... 73/572; 73/594; 73/602
[58] Field of Search ................... 73/572, 579, 594, 12, 73/584, 600, 602

[56] References Cited

U.S. PATENT DOCUMENTS

| 4,281,547 | 8/1981 | Hinshaw et al. | 73/579 |
| 4,318,302 | 3/1982 | Choi | 73/579 |
| 4,598,588 | 7/1986 | Hanson | 73/584 |
| 4,702,111 | 10/1987 | Holland | 73/579 |
| 4,858,469 | 8/1989 | Hosgood et al. | 73/579 |

OTHER PUBLICATIONS

*Mining Engineering*, Mar. 1986, p. 158 Entitled: "Bureau Develops Device to Detect Unstable Roof Rock". (Industry Newswatch).

*Primary Examiner*—Hezron E. Williams
*Assistant Examiner*—Rose M. Finley
*Attorney, Agent, or Firm*—Francis J. Mulligan, Jr.; Edward A. Steen

[57] ABSTRACT

A loose rock detector comprises an impact tool for hitting the rock face, sensors for detecting acoustic, rock motion and/or impact force signals generated by movement of the impact tool against the face of the rock, a data processor responsive to the sensors for correlating the above signals in the time and/or frequency domain against predetermined relationships to detect loose rocks and to assess mass and degree of looseness of the rock, and a display unit for displaying the results of the correlation.

7 Claims, 10 Drawing Sheets

SECTION A-A

SOUND PRESSURE (LOG SCALE)

5,024,090

LOOSE ROCK DETECTOR

TECHNICAL FIELD

This invention relates to the detection of loose rocks in hardrock mines and, once detected, to the assessment of both their mass and degree of looseness.

BACKGROUND ART

The detection of loose rock has generally been done up until now by hitting the rock with a scaling bar and listening to the resulting sounds. A "drummy" sound was an indication of loose rock and a "ringing" sound an indication of solid rock. However, the above method, although reasonably effective, proved to be highly subjective and attempts have been made to design an instrument which would be more objective. One such instrument is disclosed in U.S. Pat. No. 4,598,588 which was issued July 8, 1986 and in an article entitled "Bureau (of Mines) develops device to detect unstable roof rock" in Mining Engineering March 1986, page 158. The instrument consists of an accelerometer which is held against the rock using a spring mounted pole, and an analysing device which is held by the miner and is connected to the accelerometer by a coaxial cable. The accelerometer detects sound waves which are generated by lightly tapping the adjacent rock with a striker bar. The sound waves are received and filtered so that the energy levels of two bands — approximately 500 to 1000 Hz and 3000 to 3500 Hz — can be compared. Loose rock, relative to solid material, shows a higher energy level in the low frequency band. This is indicated by a higher number on a digital readout device. Fairly good results were obtained in identifying loose rock conditions using this instrument. However, underground testing indicated a certain amount of readout variations due to factors such as degree of contact of the accelerometer with the rock surface, the type of striker bar, the geology etc. In addition, there are several variables which affect the relative energy levels of sound waves as received by the accelerometer. For example, the dampening effect of some rock types could disguise the presence of loose rock by reducing the energy of certain frequencies and diminishing the wave energy relationship. Thus, while the primary indication of "loose/not loose" is valid under most circumstances, the specific numbers that appear on the digital readout of the instrument do not readily provide an indication of the mass of the loose rock or of the degree of looseness. The device is also limited to differentiate loose from solid if the loose is larger than 4m×0.5m×0.5m.

It is, therefore, the object of the present invention to provide a more reliable loose rock detector and also to provide a detector which can assess mass and degree of looseness of the rock.

DISCLOSURE OF INVENTION

The loose rock detector, in accordance with the present invention comprises an impact tool for hitting the rock face, sensors for detecting acoustic, rock motion and/or impact force signals generated by movement of the impact tool against the face of the rock, a data processor responsive to the above sensors for correlating such signals in the time or frequency domain against predetermined relationships to detect loose rocks and to assess mass and degree of looseness of the rock, and a display unit for displaying the results of such correlation.

The data processor comprises an analog to digital converter responsive to the sensors for converting the acoustic, motion and impact force signals from an analog to digital form, and a memory unit for storing such signals in the time domain.

The data processor also comprises a spectrum analyzer for transforming the time domain signals into the frequency domain and a computation and integration processing unit for manipulating such time domain and frequency domain signals and correlating the same against the above mentioned predetermined relationships.

BRIEF DESCRIPTION OF THE DRAWINGS

The invention will now be disclosed, by way of example, with reference to the accompanying drawings in which.

BEST MODE FOR CARRYING OUT THE INVENTION

Figure 1:
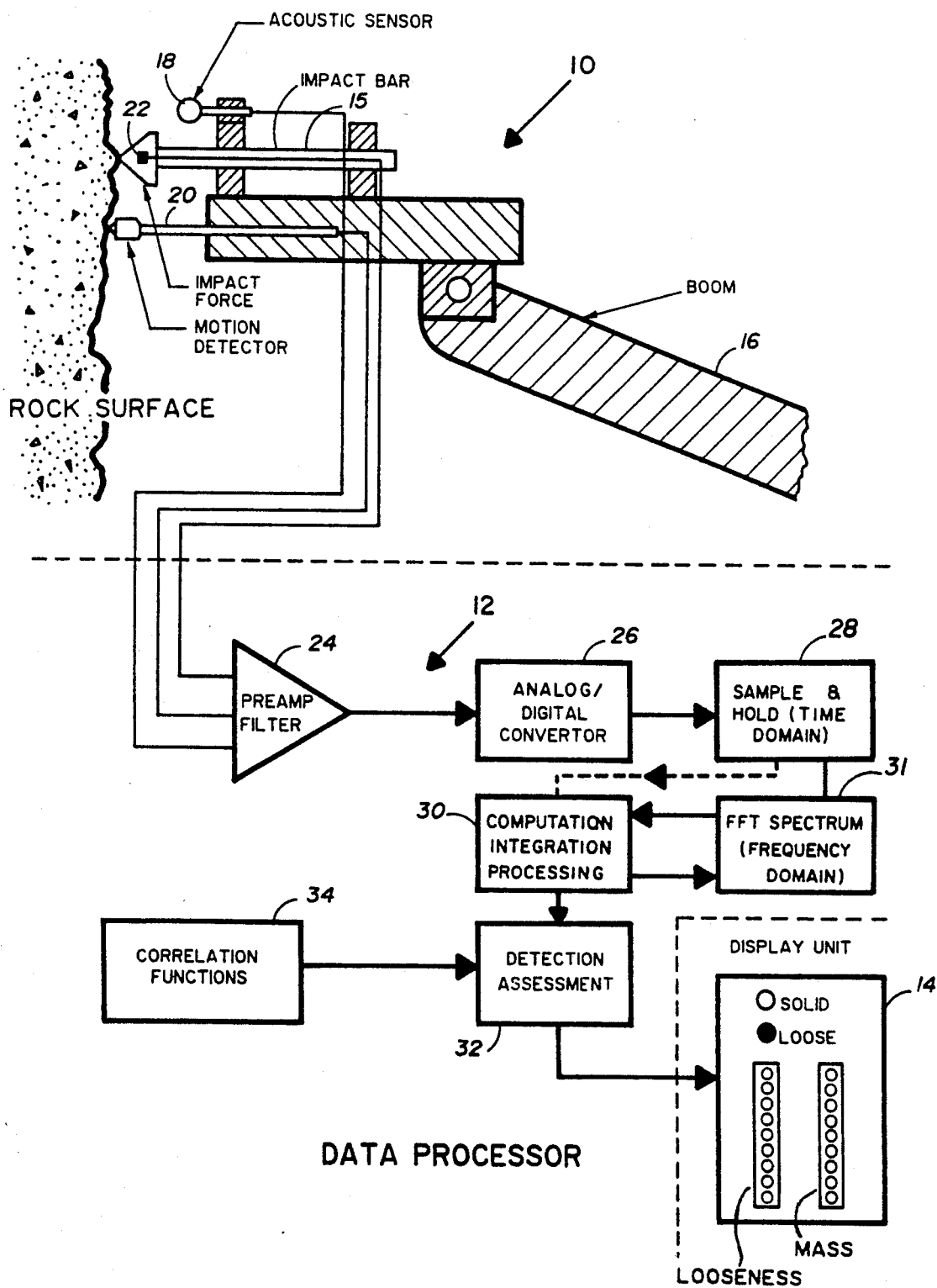
FIG. 1 is a schematic diagram of the loose rock detector in accordance with the present invention.

Referring to FIG. 1 of the drawings, the overall system to detect and assess loose rock consists of three major components: an impact tool with sensors designated generally by reference numeral 10, a data processor designated generally by reference numeral 12 and comprising electronic and computer equipment for signal analysis and correlation, and a display unit 14. The impact tool is preferably an impact bar 15 which is mounted on the boom 16 of a mechanical scaler and adapted to hit the rock face. A manually operated impact tool could also be used. The sensors associated with the impact tool consist of an acoustic sensor such as microphone 18 which is mounted at a safe distance from the rock face (typically between 100 mm and one meter), a motion sensor such as accelerometer 20 which is in contact with the rock face and an impact force sensor 22 which is attached to the impact bar. Other acoustic measuring techniques could also be used. Similarly other rock motion sensing devices could be used.

The analog signals detected by the above sensors are fed, through a preamplifier and filter 24, to an analog/digital converter 26 for conversion into a digital form and are subsequently stored into a sample and hold memory unit 28 for later analysis. The signals stored into the memory unit 28 may be analysed directly in the time domain by a computer based computation/integration processing unit 30 or converted into the frequency domain by a FFT spectrum analyser 31 prior to being analysed by the processing unit. The output of the processing unit is compared in a detection/assessment unit 32 to predetermined correlation functions 34 stored in the computer for loose rock detection and assessment of mass and degree of looseness. The functions performed by units 26, 28, 30, 31, 32 and 34 may be carried out by a properly programmed Genrad Model 2515 Computer Aided Test System (made by General Radio), although other equivalent computer aided equipment could be used. The output of the detection/assessment unit 32 is fed to the display unit 14.

Figure 2:
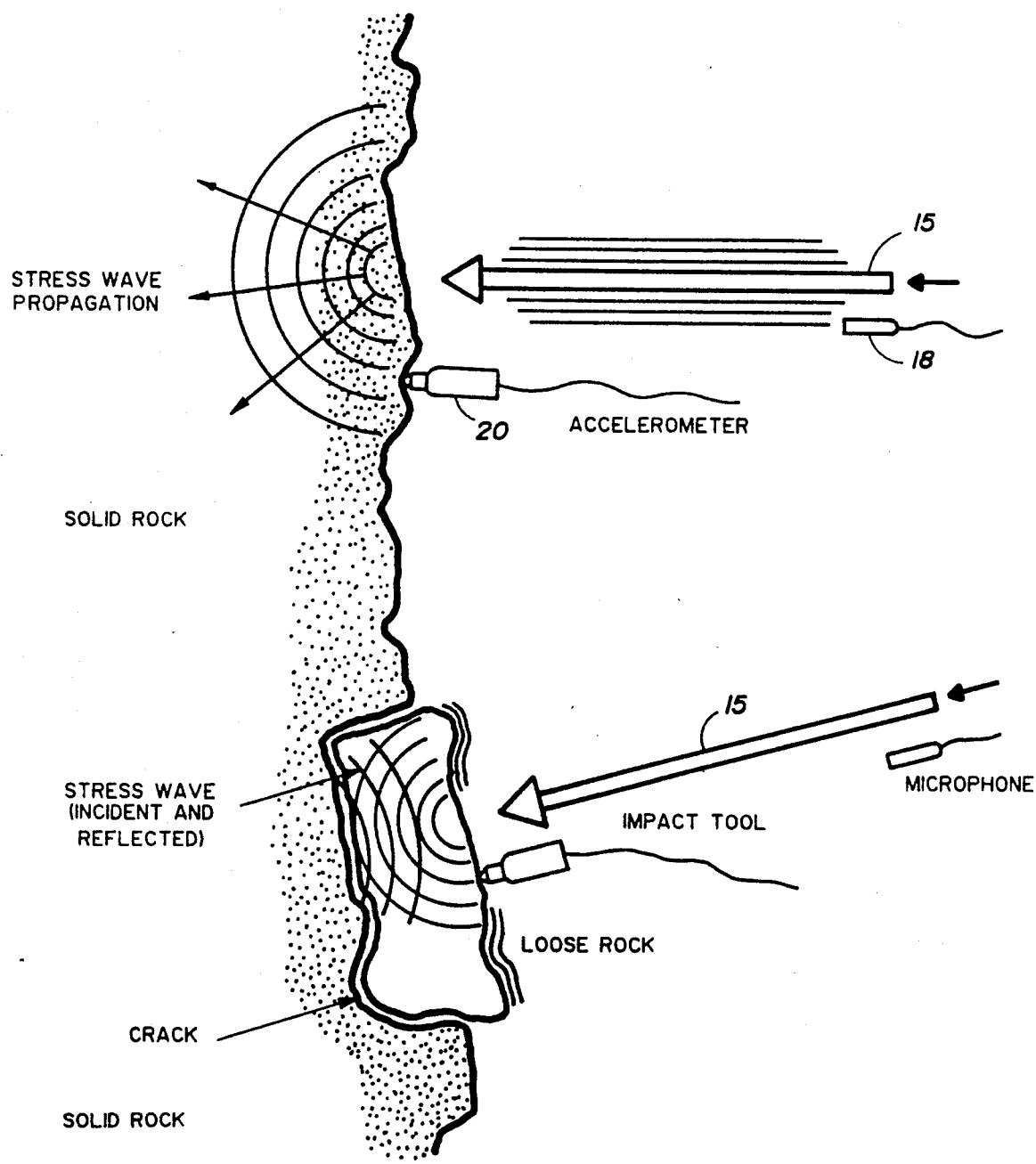
FIG. 2 is a diagram illustrating the sources of signal.

As outlined in FIG. 2, the sources of signal generated by hitting the rock surface with impact tool 15 are rock motion, impact tool vibration and incident or reflected stress waves in the rock. These signals may be in the form of acceleration signals for contact techniques using one or more sensors 20 contacting the rock surface, or in the form of acoustic signals for non-contact techniques using one or more microphones 18. Tool impact force is also detected by sensor 22 but is not shown in FIG. 2. The object of the present invention is to optimize the use of all the above signals to get the most reliable detection and quantitative assessment of mass and degree of looseness of loose rock. The signals are used in some cases separately and in other cases in combination to obtain the most reliable results.

With the non-contact technique the acoustic signals from solid rock detected by microphone 18 generally feature lower amplitude levels, low attenuation and higher frequencies typical of impact tool vibration. Conversely, the signals from loose rock show higher amplitudes, greater attenuation and lower frequency characteristics of "drummy" rocks.

Figure 3A:
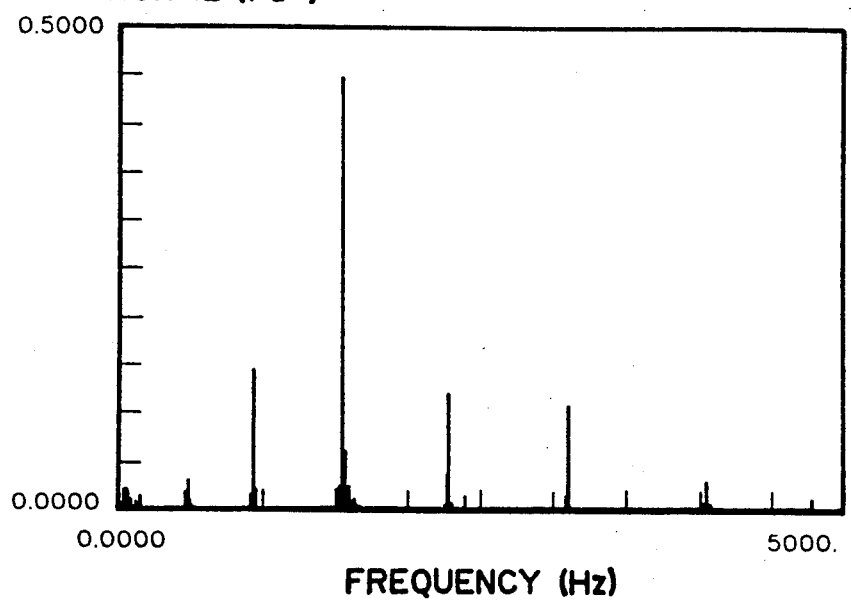
FIGS. 3a and 3b illustrate typical power spectral density diagrams of acoustic signals for solid and loose rock transformed into the frequency domain.
Figure 3B:
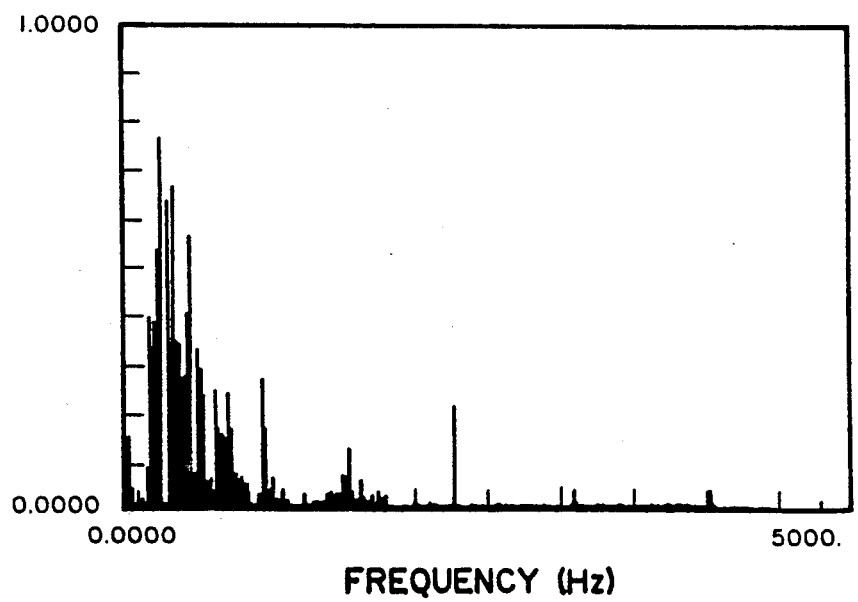

Transformed into the frequency domain, the two acoustic signals discussed above fall into very distinct categories. For solid rock, impact tool or "ringing" at well-defined natural frequencies is dominant as shown in FIG. 3a. For loose rock, lower frequency spectrum characteristics of loose rock are evident as shown in FIG. 3b. Thus frequency domain analysis of acoustic signals is appropriate to detect loose rocks.

Figure 4A:
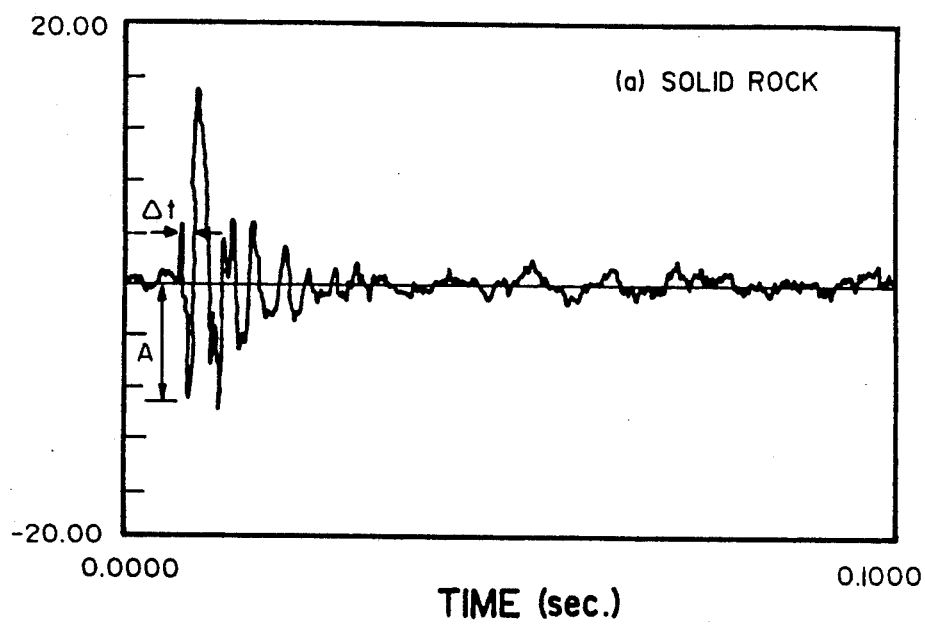
FIGS. 4a and 4b illustrate typical time domain acceleration signals for solid and loose rock.

With the contact technique, the rock acceleration response to the impact tool for solid and loose rock are measured with accelerometer 20 held in contact with the rock near the point of impact. In the time domain traces, the initial acceleration peaks tend to be higher and last longer for loose rock as evident by comparing FIGS. 4a and 4b. The first acceleration peak is also normally negative. Thus, the integrated acceleration during the time interval considered is larger for loose rock.

Figure 5A:
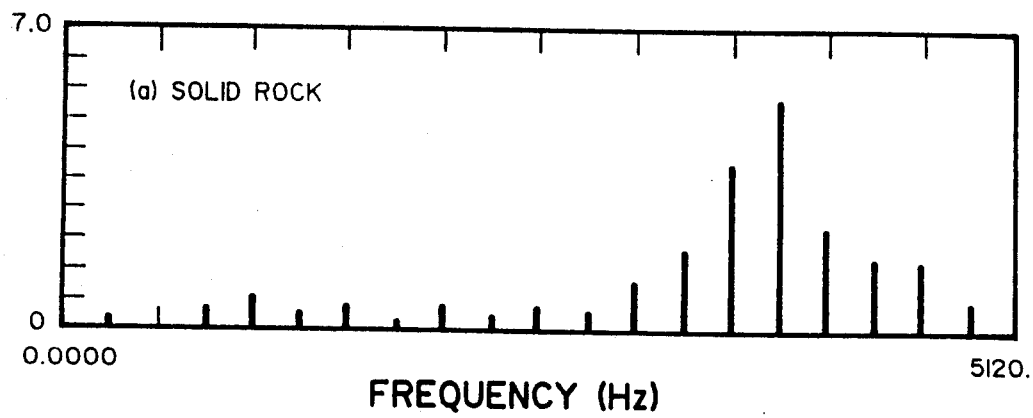
FIGS. 5a and 5b illustrate the same acceleration signals transformed into the frequency domain.
Figure 5B:
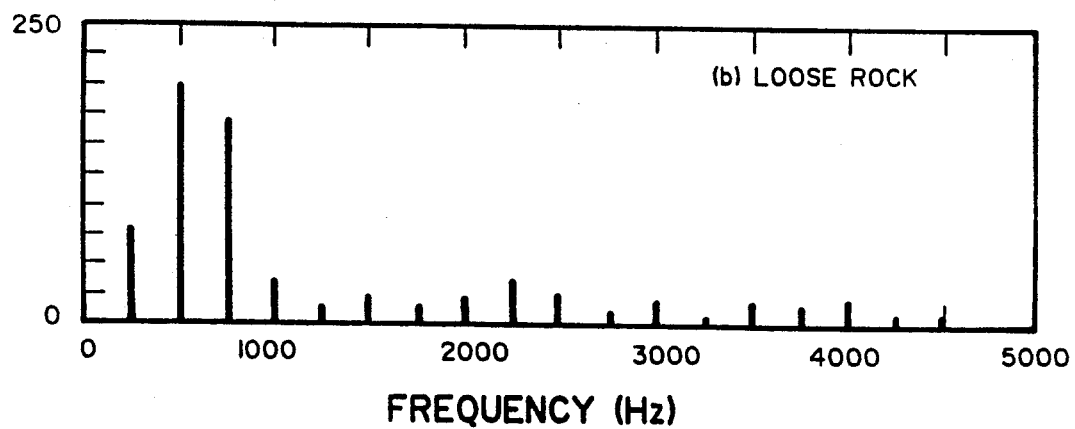

In the frequency domain, the low frequency region (i.e. 0–500 Hz) is much larger for loose rock whereas the higher frequency content (i.e. 2000–4000 Hz) tends to be higher for solid rock as shown in FIGS. 5a and 5b. Generally, the acceleration signal levels are much lower for solid rocks. This is not surprising since the only sources of signal in solid rocks are incident stress waves, whereas in loose rocks the signals also include rock body motion, rock vibration and reflected stress waves. Thus, frequency domain analysis of acceleration response signals is also appropriate for loose rock detection.

As shown above, the signals coming from loose and solid rocks exhibit significant differences. Thus, analytical techniques and comparison criteria which take advantage of these differences provide adequate information for detection of loose rock.

Loose Rock Detection

The general approach in the development of analytical techniques and criteria to detect loose rocks is to optimize the use of the available information contained in the acoustic and acceleration signals. That is: large amplitude, low frequency signals mean loose rock, lower amplitude higher frequency signals mean solid rock, vibration peaks at well defined frequencies are related to impact tool response and indicate solid rock. Several correlations or relationships have therefore been developed to formulate the above trends and characteristics as indicated below:

i) Acoustic Technique

Using the acoustic technique, the following relationships F1 has been found to be a good criterion for loose rock detection:

$$F1 = \frac{F2}{F3} = \frac{\text{(Total} - \text{Tool)Acoustic Signal (0-2000 Hz)}}{\text{Tool Acoustic Signal (0-5000 Hz)}}$$

where F2 is the total acoustic signal in the frequency range 0–2000 Hz minus the signal attributed to impact tool vibration. The tool vibration frequencies correspond to the tool natural frequencies. These natural frequencies are known and are well defined as shown by the high amplitude signals in FIG. 3a. The acoustic signals within the narrow band corresponding to the natural frequencies of the tool are subtracted from the total acoustic spectrum in a known manner. It has been found that normalization by F3, which is the sum of the acoustic signals within the narrow bands corresponding to the natural frequencies of the tool in the frequency range of 0–5000 Hz, improved the correlation. Since F3 is generally proportional to the magnitude of the impact, the above normalization essentially compensate for variation in impact force. Normalization may also be achieved directly from the impact force measurement. The discrimination between loose and solid rock given by F1 is good. For example, in tests conducted in a mining environment, F1 <0.34 was characteristic of solid rock and F1 >0.55 was characteristic of loose rock. These values are used as a reference in the correlation function unit 34 for comparison against the actual measurements.

Other relationships and criteria may be used to enhance detection reliability. For example, F2< preset level, which depends on such parameters as the impact force or acoustic sensor characteristics, has been used as a secondary criterion. With the two criteria, correct assessment for 94 out of 95 rock samples taken in a mine has been achieved. Additional relationships could also be used to improve the reliability further.

ii) Contact Technique

Similarly, loose rock detection criteria were developed for the contact technique. Relationship F4, which is the integral of the Power Spectral Density of the acceleration signal (shown in FIG. 5b) in the frequency range 125–375 Hz is a good indication of looseness. It makes sense that rock motion be related to looseness.

This relationship can be used as the primary criterion for loose rock detection.

Figure 4B:
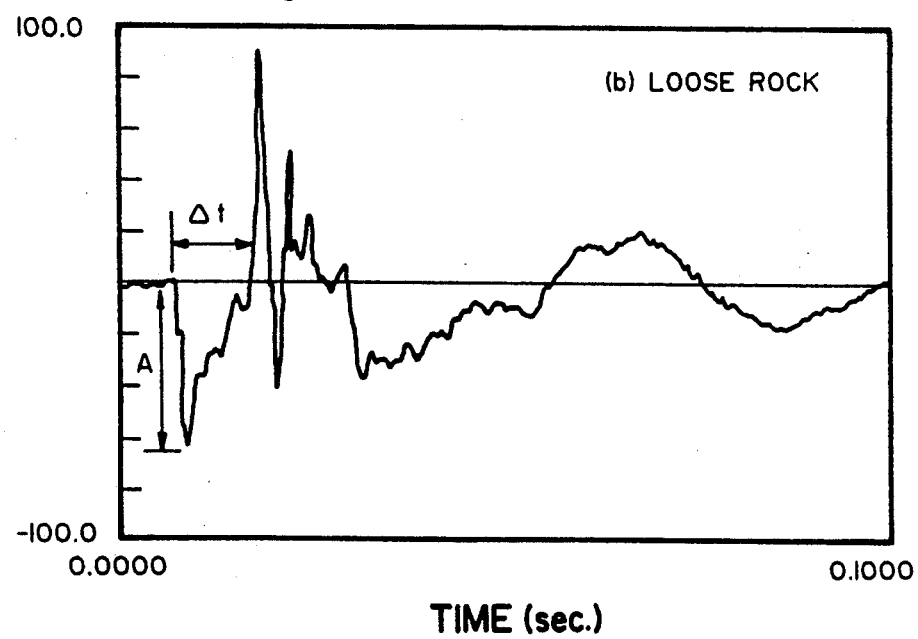

It has been found in some cases that the first acceleration peak is positive instead of negative as shown in FIG. 4b. This happens only for loose rock and may be attributed to some rocking-type motion of the rock sample. A positive peak means that, when the rock is hit into the wall by the impact tool, it moves away from the wall at the accelerometer location a short distance away, indicating that the rock is pivoting around support between the point of impact and the accelerometer. Another possible explanation is the presence of a stress wave reflected by a crack or a fault in the rock. This behavior can only occur for loose rock. Hence, a positive first acceleration peak is also a useful criterion for loose rock detection. Note that this is a time domain criterion.

The above multiple criterion also leads to a success rate better than 95% for the contact technique (in fact correct assessment for 64 out of 65 samples in tests conducted in a mining environment).

Rock Mass Assessment i) Acoustic Techniques

Figure 6A:
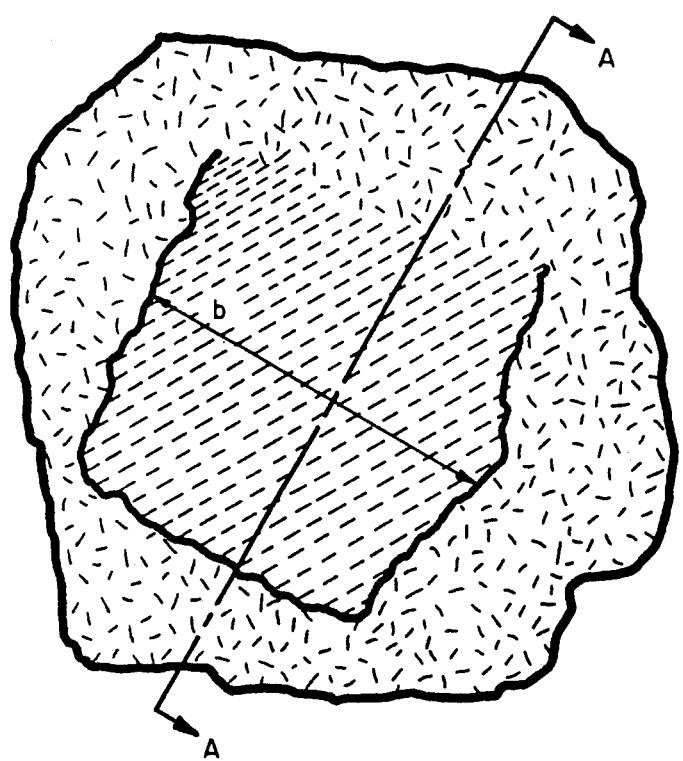
FIGS. 6a and 6b are diagrams illustrating an idealized loose rock.
Figure 6B:
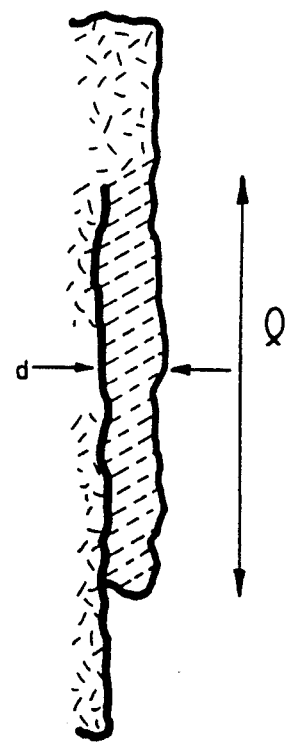

It has been found that there is some correlation between low frequency acoustic signal levels (i.e. 0-500 Hz) and rock mass. The average rock response frequency appeared to decrease with rock cantilevered length. This may be explained by the following analysis:

The frequency, f, of the idealized cantilevered loose rock of FIGS. 6a and 6b may be expressed by:

$$f^2 \alpha \frac{EI}{ml^4}$$

where the flexural rigidity EI is related to $bd^3$, the mass per unit length m is related to bd, and l is the cantilevered length of the rock. Thus $$f \alpha d/l^2$$

Since the aspect ratio of loose rock, d/l, is on the average roughly constant, then $$f \alpha 1/l$$

which means that frequency should decrease with size. Thus a rock size correlation with frequency emerges. A convenient way to represent this correlation is the low frequency acoustic signal relationship F5 which is the amplitude of low frequency sound from the rock below 500 Hz. This is essentially the integral of the Power Spectral Density of the acoustic signal (shown in FIG. 3b) over the frequency range 0-500 Hz.

Figure 7:
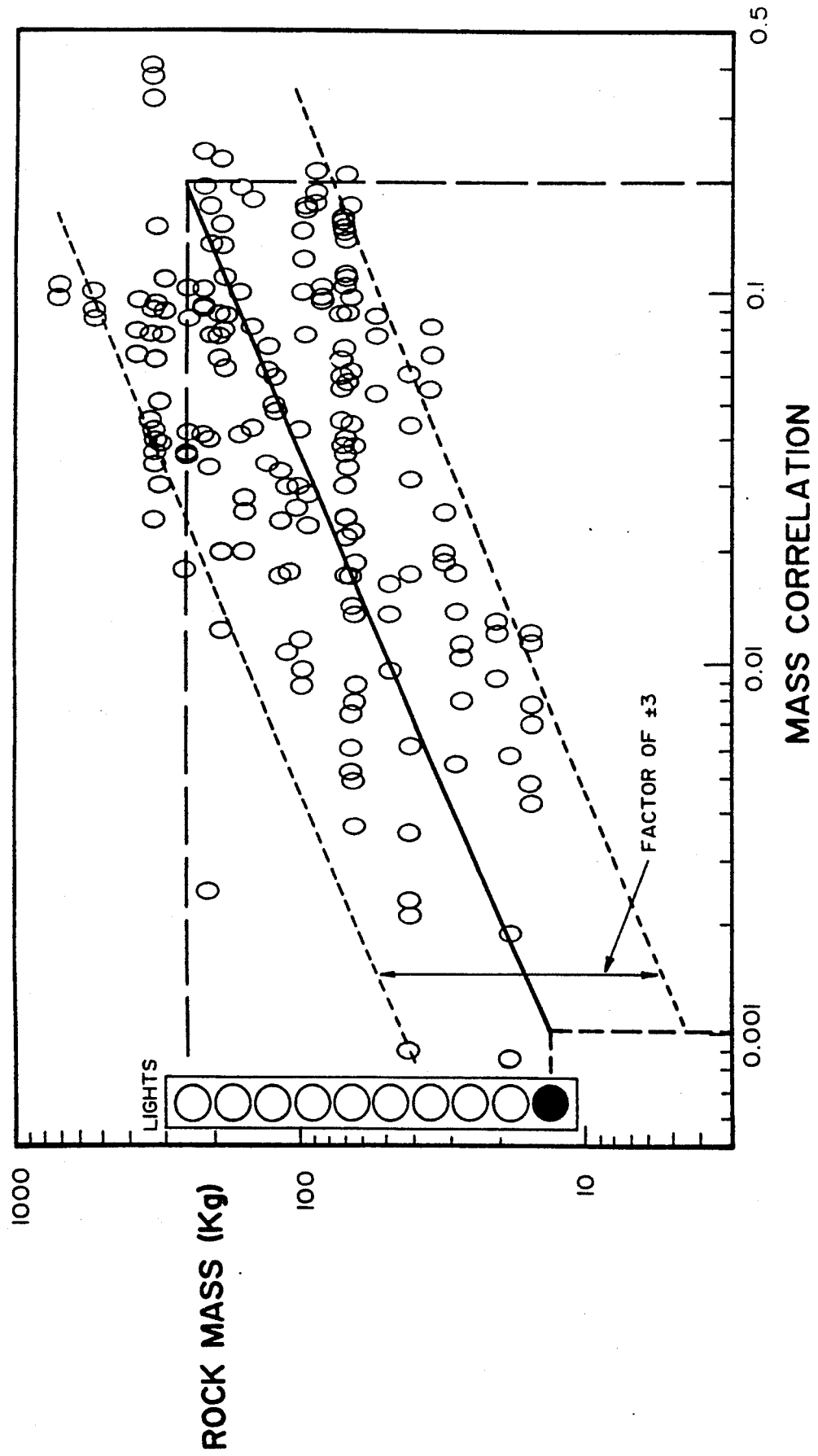
FIG. 7 illustrates a correlation which has been developed for mass assessment using acoustic and impact force signals.

It was found desirable to normalize F5 by dividing it by the impulse signal F6 which is the integral of impact force during the time the impact tool is contacting the rock. The resulting mass correlation is F7=F5/F6 as shown in FIG. 7. This relationship has been developed during test done on several rock samples of known mass. Most of the data is within a factor of ±3 of a best fit line through the experimental data. The best fit line is used as a criterion to assess rock mass in correlation function unit 34. In practice, the assessment is displayed with bar lights in display unit 14 of FIG. 1.

ii) Contact Technique

From basic principle, it is expected that rock mass, M, is inversely proportional to rock acceleration a(t) for a given impact force F(t). Thus, if the impact momentum is roughly constant, then the rock mass should correlate with $$M \alpha 1/a(t)$$

Figure 8:
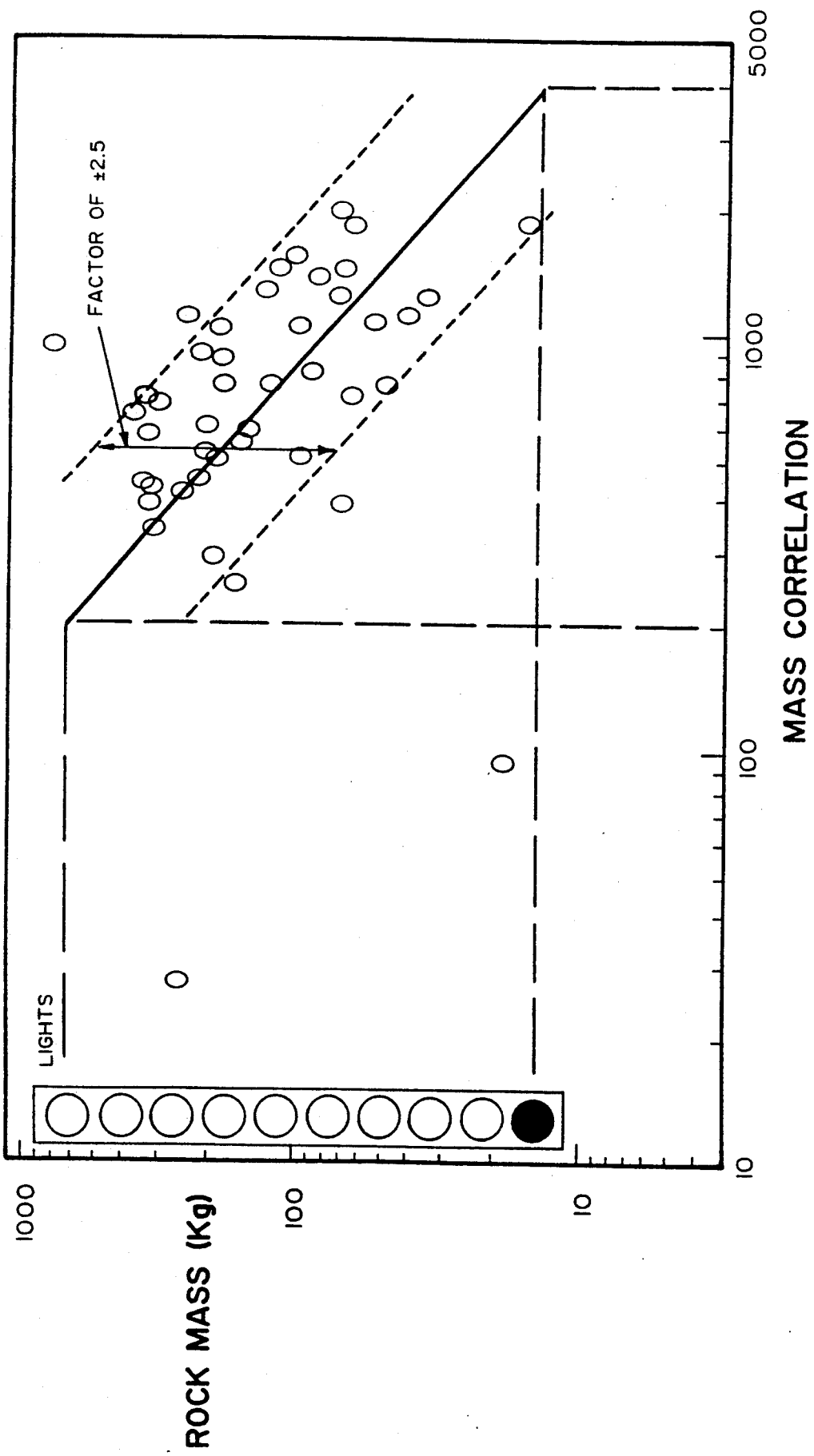
FIG. 8 illustrates a correlation which has been developed for mass assessment using acceleration signals.

The maximum rock acceleration relationship, called F8, is found to correlate well against rock mass as shown in FIG. 8. The agreement between predicted and measured rock mass is roughly within a factor of ±2.5. The best fit line through the experimental data is a criterion to assess rock mass which is used in correlation function unit 34.

Degree of Looseness Assessment

The physical characteristics of looseness are cracks and clearances which permit relative motion between the loose rock and the underlying solid rock. As a loose rock moves, there will likely be significant rubbing and impacting at these cracks and clearances which absorb energy, causing the rock motion to decay quickly after being struck. Less loose rocks are attached-better and so will have less energy absorption capability. Thus it makes sense that the degree of looseness be proportional to damping.

Figure 9:
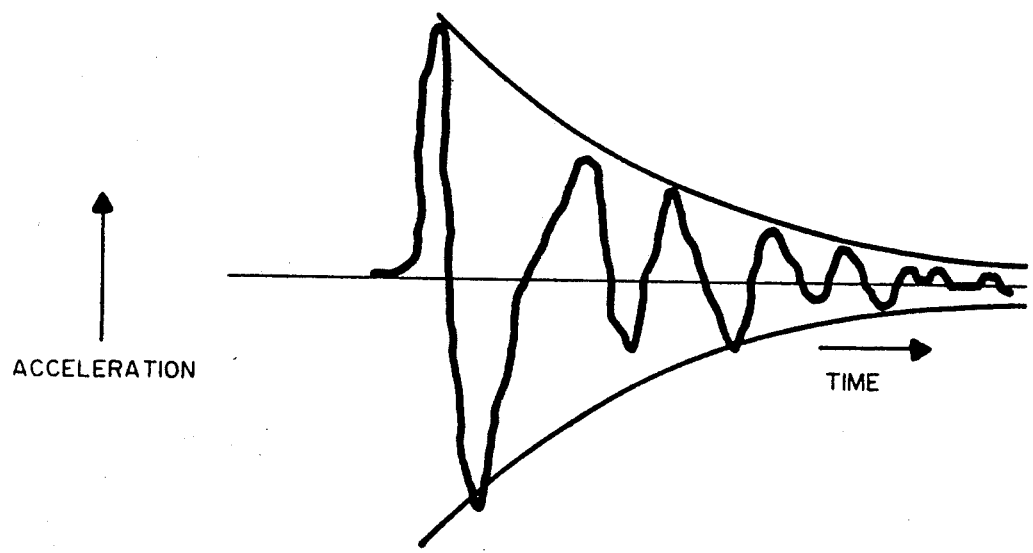
FIG. 9 illustrates a typical time domain acceleration signal from a loose rock.

Some of the features of a typical time domain signal from a loose rock are shown in FIG. 9. When the tool hits the rock, it vibrates in and out with a decreasing amplitude. The rate of decay of the signals has been found to be a good indication of degree of looseness. Calculation of this rate of decay, termed damping uses many different techniques. The basic objective is to fit an exponentially decaying function to the signal as shown in FIG. 9.

Because we are interested only in the damping of the sound produced by rock motion, not that from tool vibration, the frequency lines corresponding to the known natural frequencies of the tool are removed in the frequency domain. To create a time domain signal containing only the sound produced by rock motion, the spectrum is transformed back into the time domain.

Figure 10:
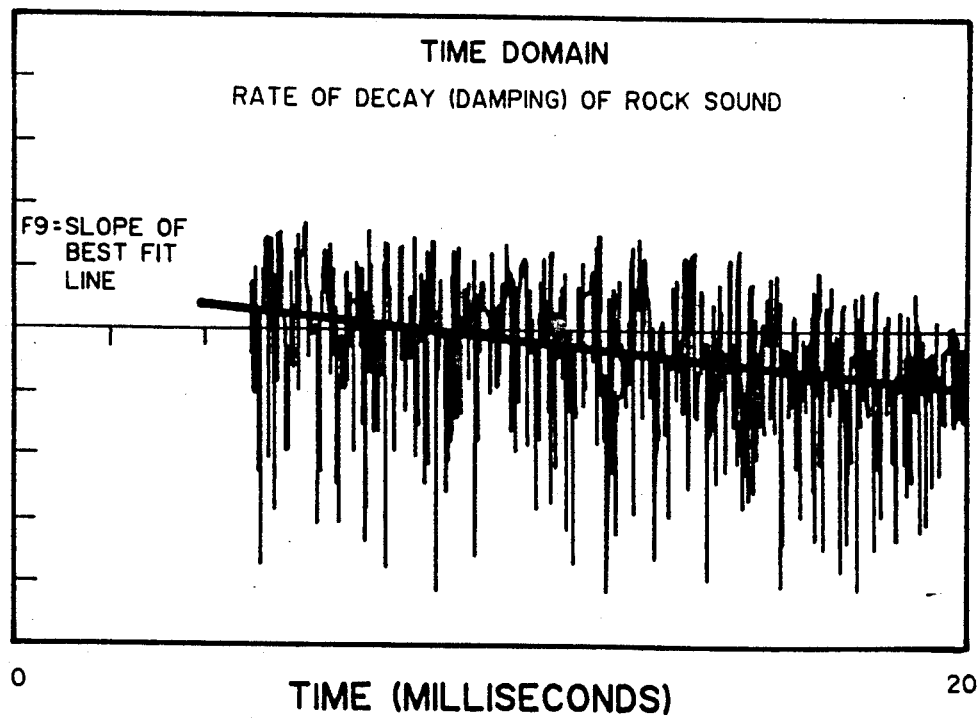
FIG. 10 illustrates how a typical time domain acoustic signal may be used to calculate rock damping.

Simple structures often vibrate with a discrete frequency, which results in a clean decaying sinusoidal signal following an impulse. Damping can be calculated by comparing the relative amplitude of successive peaks. In the case of loose rock, the signal is very "noisy" looking because of the complicated geometry and support conditions. To determine damping from a noisy signal, the following procedure was used:
1. The absolute value of the rock sound pressure is calculated as shown in FIG. 10.
2. A very small value is added to eliminate low values on the log scale.
3. The slope of the best fit line through the data is calculated.

This is equivalent to fitting a curve of the following form through the data.

$$\text{amplitude} = \text{constant} \times \exp^{-(\text{rate of decay}) \times \text{time}}$$

The slope of the line is equal to the rate of decay or damping.

The most successful looseness correlation which was developed using acoustic signals is F9=Rate of decay of rock sound. The degree of looseness was found to be proportional to the value of F9. Many rock samples were tested and a best fit line through the experimental data was derived as for F7 and F8. The best fit line is used as a criterion to assess degree of looseness in correlation function unit 34. In practice, the degree of looseness is indicated by the bar lights in display device 14 of FIG. 1. The number of lights that would be turned on for a given value of F9 is related to looseness. A corresponding relationship F10 was developed using acceleration signals.

Figure 11:
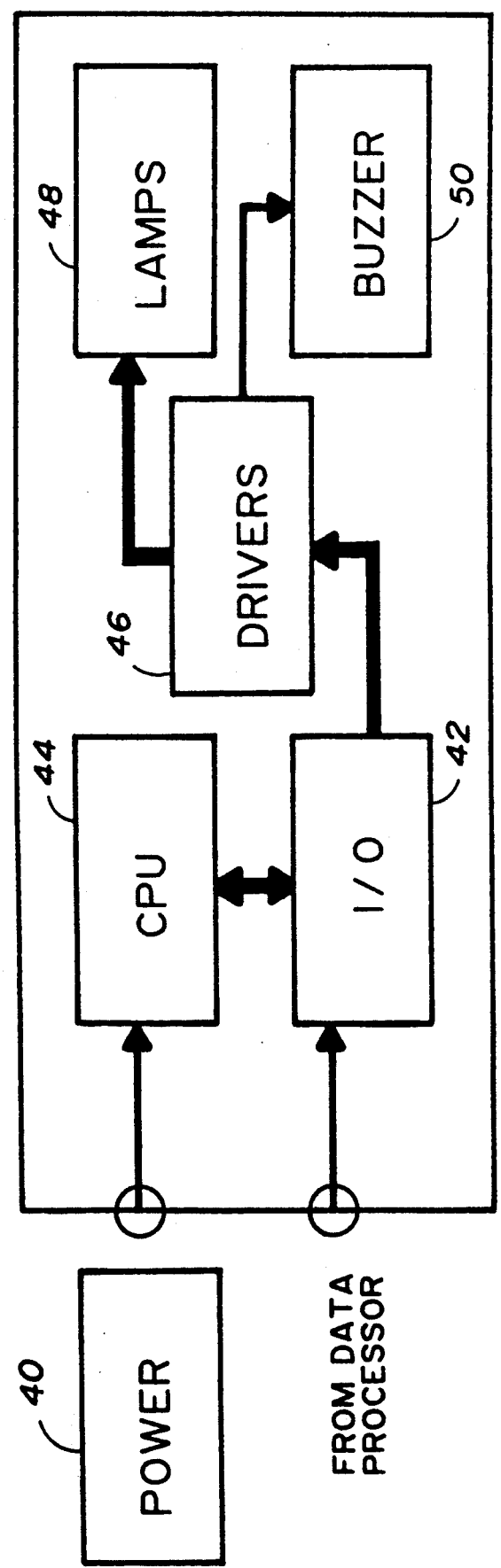
FIG. 11 is a block diagram of a suitable display device.

FIG. 11 is a block diagram of a display device 14 which is powered by power source 40. The display device comprises an I/O unit 42 which under the control of a CPU unit 44 receives the signals from the data processor and operates conventional drivers 46 for energizing the various lamps 48 of the bar chart and a buzzer 50 of the display unit.

We claim:

1. A loose rock detector comprising:
   a) an impact tool for hitting the rock face;
   b) at least one sensor responsive to vibrations generated in the rock and in the impact tool by movement of said impact tool against the face of the rock for generating acoustic signals representative of said vibrations;
   c) a data processor responsive to said signals for correlating said signals in the frequency domain against a predetermined relationship to detect loose rocks, said relationship being $F1 \times F2/F3$, where F2 is the sum of the amplitude of the acoustic signals attributed to both the rock and impact tool vibrations in a frequency range of 0–2000 Hz minus the sum of the amplitude of the acoustic signal attributed to impact tool vibration, and F3 is the sum of the amplitude of the acoustic signal attributed to impact tool vibration in a frequency range of 0–5000 Hz; and
   d) a display unit for displaying the results of the correlation.

2. A loose rock detector comprising:
   a) an impact tool for hitting the rock face;
   b) at least one sensor responsive to vibrations generated in the rock by movement of said impact tool against the face of the rock for generating rock motion signals representative of said vibrations;
   c) a data processor responsive to said signals for correlating said signals in the frequency domain against a predetermined relationship to detect loose rock, said relationship being F4, which is the integral of the power spectral density of the rock motion signals in a frequency range of 125–375 Hz; and
   d) a display unit for displaying the results of the correlation.

3. A loose rock detector as defined in claims 1 or 2 wherein at least one additional criterion in the frequency of time domain is used to improve reliability of detection.

4. A loose rock detector comprising:
   a) an impact tool for hitting the rock face and having means for measuring impact force and producing a signal indicative thereof;
   b) at least one sensor responsive to vibrations generated in the rock by movement of said impact tool against the face of the rock for generating acoustic signals representative of said vibrations;
   c) a data processor responsive to said signals for correlating said signals in the frequency domain against a predetermined relationship for mass assessment of loose rock, said relationship being $F7 \times F5/F6$, where F5 is the amplitude of low frequency acoustic signals from the rock below 500 Hz, and F6 is the integral of the impact force during the time the impact tool is contacting the rock; and
   d) a display unit for displaying the results of the correlation.

5. A loose rock detector comprising:
   a) an impact tool for hitting the rock face and having means for measuring impact force and producing a signal indicative thereof;
   b) at least one sensor responsive to vibrations generated in the rock by movement of said impact tool against the face of the rock for generating rock motion signals representative of said vibrations;
   c) A data processor responsive to said signals for correlating said signals against a predetermined relationship F8 for mass assessment of loose rock, said relationship being that loose rock mass is inversely proportional to rock acceleration for a given impact force; and
   d) a display unit for displaying the results of the correlation.

6. A loose rock detector comprising:
   a) an impact tool for hitting the rock face;
   b) at least one sensor responsive to vibrations generated in the rock by movement of said impact tool against the face of the rock for generating acoustic signals representative of said vibrations;
   c) a data processor responsive to said signals for correlating said signals in the time domain against a predetermined relationship for degree of looseness assessment of loose rock, said relationship being $F9 \times$ rock acoustic signal damping; and
   d) a display unit for displaying the results of the correlation.

7. A loose rock detector comprising:
   a) an impact tool for hitting the rock face;
   b) at least one sensor responsive to vibrations generated in the rock by movement of said impact tool against the face of the rock for generating rock motion signals representative of said vibrations;
   c) a data processor responsive to said signals for correlating said signals in the time domain against a predetermined relationship for degree of looseness assessment of loose rock, said relationship being $F10 \times$ rock acceleration signal damping; and
   d) a display unit for displaying the results of the correlation.

* * * * *

UNITED STATES PATENT AND TRADEMARK OFFICE
CERTIFICATE OF CORRECTION

PATENT NO. : 5,024,090

DATED : June 18, 1991

INVENTOR(S) : Michael J. Pettigrew, et al

It is certified that error appears in the above-identified patent and that said Letters Patent is hereby corrected as shown below:

Column 7, claim 1, line 31, "F1xF2/F3" should read --F1= F2/F3--.

Column 8, claim 4, line 12, "F7xF5/F6" should read --F7= F5/F6--;
        claim 6, line 45, "F9xrock" should read --F9= rock--;
        claim 7, line 58, "F10xrock" should read --F10= rock--.

Signed and Sealed this

Seventeenth Day of November, 1992

Attest:

DOUGLAS B. COMER

Attesting Officer      Acting Commissioner of Patents and Trademarks